(12) United States Patent
Son

(10) Patent No.: US 9,557,309 B2
(45) Date of Patent: Jan. 31, 2017

(54) PEN TYPE OF APPARATUS FOR MEASURING MULTIPLE WATER QUALITIES

(71) Applicant: Yun-Ho Son, Seoul (KR)

(72) Inventor: Yun-Ho Son, Seoul (KR)

(*) Notice: Subject to any disclaimer, the term of this patent is extended or adjusted under 35 U.S.C. 154(b) by 162 days.

(21) Appl. No.: 14/256,553

(22) Filed: Apr. 18, 2014

(65) Prior Publication Data

US 2015/0226721 A1 Aug. 13, 2015

(30) Foreign Application Priority Data

Feb. 10, 2014 (KR) .................. 10-2014-0014686

(51) Int. Cl.
| | | |
|---|---|---|
| *G01N 33/18* | (2006.01) | |
| *G01N 27/06* | (2006.01) | |
| *G01N 27/416* | (2006.01) | |
| *G01N 27/12* | (2006.01) | |
| *G01N 27/48* | (2006.01) | |
| *G01N 27/22* | (2006.01) | |

(52) U.S. Cl.
CPC .............. *G01N 33/18* (2013.01); *G01N 27/06* (2013.01); *G01N 27/4167* (2013.01); *G01N 27/121* (2013.01); *G01N 27/223* (2013.01); *G01N 27/48* (2013.01)

(58) Field of Classification Search
CPC .. G01N 27/048; G01N 27/121; G01N 27/223; G01N 33/246; A61F 13/42
USPC ......................................... 324/694
See application file for complete search history.

(56) References Cited

U.S. PATENT DOCUMENTS

| | | | | |
|---|---|---|---|---|
| 2,456,117 A * | 12/1948 | Feller | ..................... | G01N 27/06 324/445 |
| 3,990,066 A * | 11/1976 | Malmgren | ............ | G01N 27/10 210/85 |
| 5,199,639 A * | 4/1993 | Kobayashi | ........... | B05B 1/1645 239/11 |
| 5,821,405 A * | 10/1998 | Dickey | .................. | G01D 11/24 73/170.29 |
| 6,083,405 A * | 7/2000 | Tanaka | ...................... | C02F 1/28 210/170.05 |
| 6,269,320 B1 * | 7/2001 | Otto | ........................ | B64D 15/20 244/134 C |
| 6,938,506 B2 * | 9/2005 | Henry | .................... | G01D 11/24 73/866.5 |
| 8,419,912 B2 * | 4/2013 | Sagawa | ............. | G01N 27/4168 204/400 |
| 2007/0084722 A1 * | 4/2007 | Sagawa | ............. | G01N 27/4168 204/403.01 |
| 2008/0264788 A1 * | 10/2008 | Uthemann | .......... | G01N 27/283 204/412 |

FOREIGN PATENT DOCUMENTS

| | | |
|---|---|---|
| KR | 100865639 B1 | 10/2008 |
| KR | 100874779 B1 | 12/2008 |

* cited by examiner

*Primary Examiner* — Patrick Assouad
*Assistant Examiner* — Christopher McAndrew
(74) *Attorney, Agent, or Firm* — Kaplan Breyer Schwarz & Ottesen, LLP

(57) ABSTRACT

Provided is a pen type of apparatus for measuring multiple water qualities, which is capable of measuring acidity (pH) and electric conductivity (EC) without interfering with each other in agricultural water for hydroponic cultivation to easily confirm the measured results.

3 Claims, 7 Drawing Sheets

United States Patent US 9,557,309 B2

PEN TYPE OF APPARATUS FOR MEASURING MULTIPLE WATER QUALITIES

CROSS-REFERENCE TO RELATED APPLICATION

This application claims priority to and the benefit of Korean Patent Application No. 10-2014-0014686, filed on Feb. 10, 2014, the disclosure of which is incorporated herein by reference in its entirety.

BACKGROUND OF THE INVENTION

Field of the Invention

The present invention relates to an apparatus for measuring a water quality, and more particularly, to a pen type of apparatus for measuring multiple water qualities, which is capable of measuring acidity (pH) and electric conductivity (EC) without interfering with each other in agricultural water for hydroponic cultivation to easily confirm the measured results.

Description of the Related Art

The contamination of water today caused by municipal sewage and industrial wastewater not only destroys ecosystems, but is becoming a serious social concern by causing the depletion of water for industry and agriculture and water resources needed for drinking water. For example, while underground water is still clean, thoughtless development is leading to its accelerated depletion and contamination.

Recently, however, as awareness has gradually grown on the importance of managing and using water resources, various management systems for preventing the contamination of water resources and efficiently using them are being developed and implemented, so that water resources can not only be used for industry, but for household drinking water and water for living, and various other uses.

Meanwhile, modern living environments are becoming increasingly eco-friendly, whereby hydroponic techniques are becoming widespread in many households which directly cultivate hydroponic plants indoors such as immature stemmed plants or organic vegetables, and small fruit-bearing plants, and various types of household aquariums are being installed to control indoor temperature and humidity. In such cases, the individual households need to be supplied with water with a suitable level of quality for raising the hydroponic plants or the aquarium fish, and users need to personally manage the water to maintain it in an optimal state.

That is, in order to provide suitable growing conditions for a normal household to cultivate hydroponically or keep an aquarium, the quality of water used for this purpose must be continuously measured and managed in terms of water level, temperature, acidity, and electric conductivity (EC). It is particularly important that water used for hydroponics or an aquarium be measured and managed in terms of acidity (pH or hydrogen ion concentration) and EC or Total Dissolved Solids (TDS) characteristics. To this end, various types of water quality measuring devices have been disclosed so as to be easily used even by normal households. For example Korean Registered Patent No. 10-0874779 (Cited Patent Document 1) discloses a hydrogen ion concentration measuring device, and Korean Registered Patent No. 10-0865639 (Cited Patent Document 2) discloses an electric conductivity measuring device.

Also, multipurpose water quality measuring devices have recently been introduced that can measure both acidity and electric conductivity. FIG. 1 is a schematic perspective view illustrating the general structure of a multipurpose water quality measuring device according to the related art, which was developed by the present applicant. As illustrated, a water quality measuring device 10 of the related art is configured of a bar-shaped housing 11 having a predetermined length, a measuring unit 12 provided on one side of the housing 11, and a display unit 13 and a user input unit 14 provided on an outer surface of the housing 11. A protective cap 15 for protecting a sensor of the measuring unit 12 is provided on one side of the housing. Also, while not shown, a control unit for measuring and displaying acidity and electric conductivity is provided together with a power supply unit within the housing 11.

While various methods may be employed for measuring acidity and electric conductivity using a multipurpose water quality measuring device, in general, a method is used of taking measurements using a voltage that is output according to changes in the hydrogen ion concentration inside and outside a hydrogen sensitive glass bulb, and for electric conductivity, a technique is used in which a current is applied between positive and negative electrodes and the resistance that occurs across a solution in the water being measured is used. To this end, the measuring unit 12 provided on one side of the water quality measuring device 10 is configured of a pH sensor electrode 12a for measuring acidity, an EC sensor electrode 12b for measuring electric conductivity, and a temperature sensor 12c for measuring the temperature of the water being measured.

While such a water quality measuring device has the advantage that one device may be used to measure both acidity and electric conductivity, it involves the limitation that the pH sensor electrode 12a and the EC sensor electrode 12b are disposed close together so that interference occurs between the two sensor electrodes. Specifically, when the pH sensor electrode 12a and the EC sensor electrode 12b are immersed in the same water being measured, both sensor electrodes simultaneously contact the water being measured and cause interference therebetween.

In detail, the pH sensor electrode 12a is configured of a measuring electrode within the glass bulb and a reference electrode outside the glass bulb, and measurements are taken by discharging a flow of an electrolyte solution such as potassium chloride (KCl) from the reference electrode. At this point the potassium chloride flowing out from the pH sensor electrode 12a side is dissolved in the water being measured and changes the resistance of the water being measured so that an inaccurate value is measured by the EC sensor electrode 12b when the electric conductivity is measured.

Additionally, when the water quality measuring device is stored, the pH sensor electrode 12a needs to always be maintained in a state of wet contact with the electrolyte solution (KCl), while the EC sensor electrode, on the other hand, 12b needs to be kept in a clean state. Thus, when the electrolyte solution on the pH sensor electrode 12a side contacts the EC sensor electrode 12b and contaminates the EC sensor electrode 12b, the inconvenience arises of having to wash the EC sensor electrode 12b for each use in order to maintain the clean state thereof and produce accurate electric conductivity measurements.

SUMMARY OF THE INVENTION

Accordingly, the present invention is directed to a pen type of apparatus for measuring multiple water qualities, which is capable of measuring acidity and electric conductivity of water to be measured by using one apparatus without interfering with each other that substantially obviates one or more problems due to limitations and disadvantages of the related art.

The present invention is also directed to a pen type of apparatus for measuring multiple water qualities, in which a display part for displaying a measured value is synchronized in a direction of each of measuring sensors for measuring to automatically change a direction of a display, thereby easily confirming the result measured in each of measuring modes.

According to an aspect of the present invention, there is provided a pen type of apparatus for measuring multiple water qualities, the apparatus including: a housing having an accommodation space therein and a predetermined length; a first measuring module disposed on one end of the housing in a longitudinal direction to measure a first characteristic of water to be measured; a second measuring module disposed on the other end of the housing in the longitudinal direction to measure a second characteristic of the water to be measured; an inclination direction detection sensor accommodated in the housing to detect an inclined direction of the housing; a display module disposed on an outer circumferential surface of the housing to display values measured by the first and second measuring modules, wherein a first display unit for displaying the value measured by the first measuring module is disposed in one direction, and a second display unit for displaying the value measured by the second measuring module in the other opposite direction to overlap each other; and a control module accommodated in the housing to control measuring operations of the first and second measuring modules according to the inclined direction of the housing, which is detected by the inclination direction detection sensor, the control module controlling the display module so that each of the values measured by the first and second measuring modules is displayed on the display module through the first or second display unit.

The first measuring module may include an acidity measuring module for measuring acidity of the water to be measured, and the second measuring module may include an electric conductivity measuring module for measuring electric conductivity of the water to be measured.

The inclination direction detection sensor may include a gyro sensor.

The apparatus may further include a manipulation unit disposed on the outer circumferential surface to input a user command.

DETAILED DESCRIPTION OF THE INVENTION

The present invention and the technical objects achieved by the embodiment of the present invention will be clear by the exemplary embodiments that are described below. Exemplary embodiments of the present invention will be described below in more detail with reference to the accompanying drawings.

Figure 1:
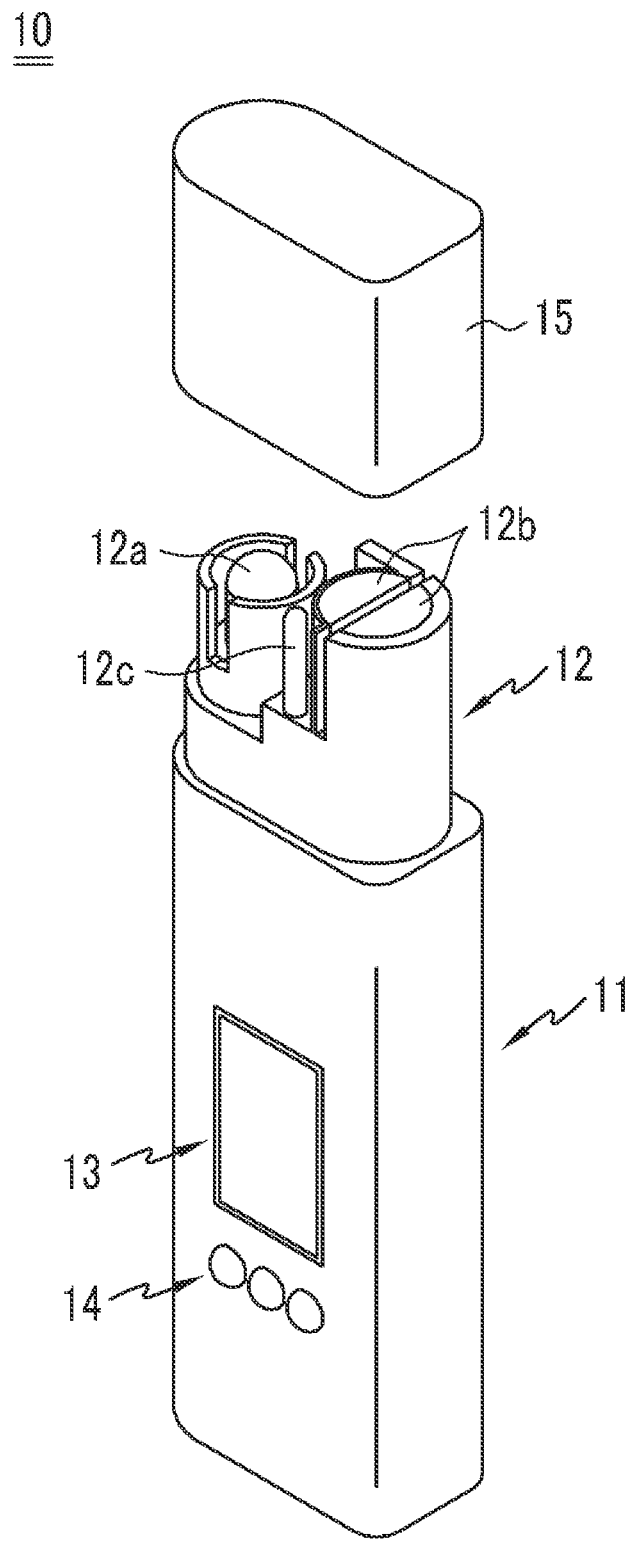
FIG. 1 is a perspective of a water quality measuring apparatus according to a related art.
Figure 2:
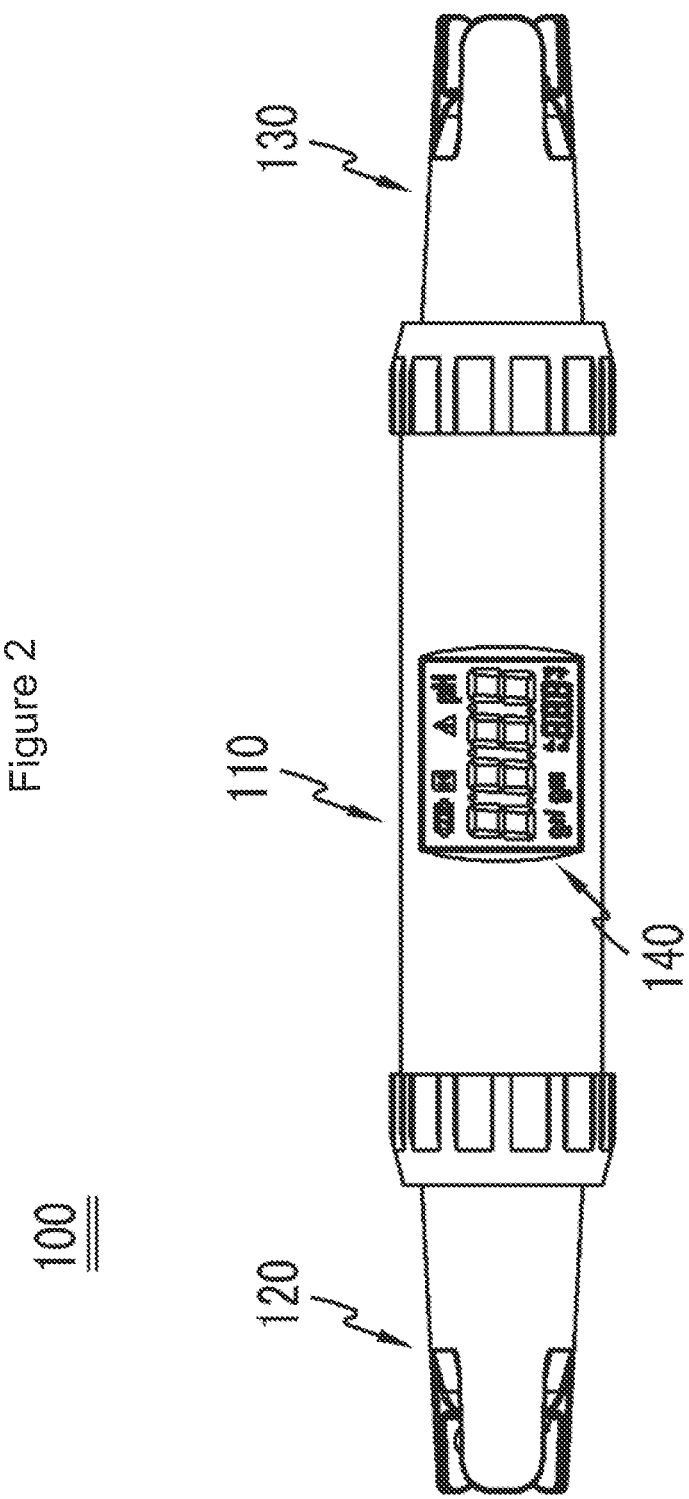
FIG. 2 is a front view of a water quality measuring apparatus according to an embodiment of the present invention.
Figure 3:
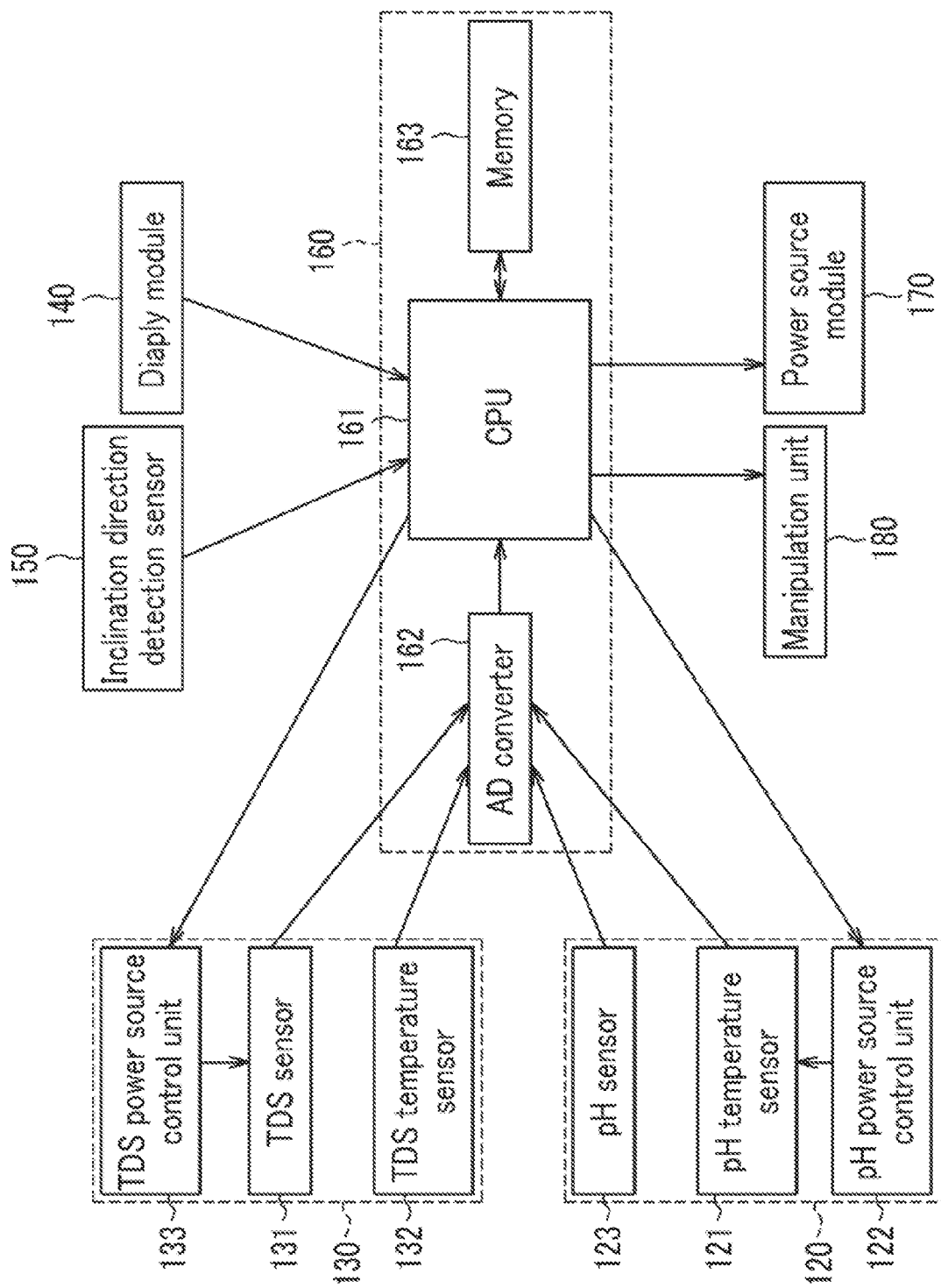
FIG. 3 is a block diagram illustrating constitutions of the water quality measuring apparatus according to an embodiment of the present invention.
Figure 4A:
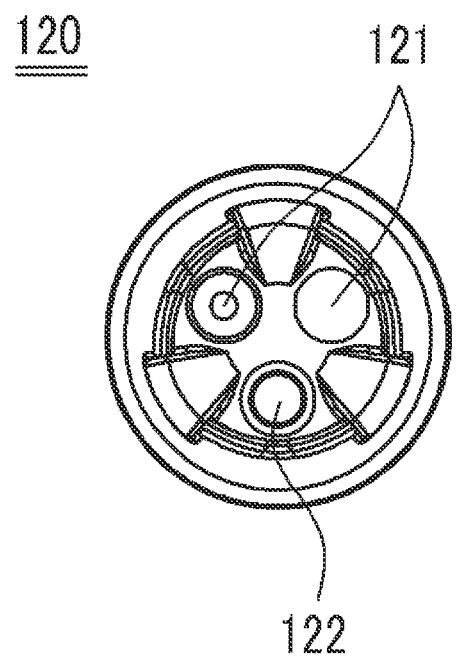
FIGS. 4A and 4B are side views of an acidity measuring module and an electric conductivity measuring module, respectively, which are main parts of FIG. 2.
Figure 4B:
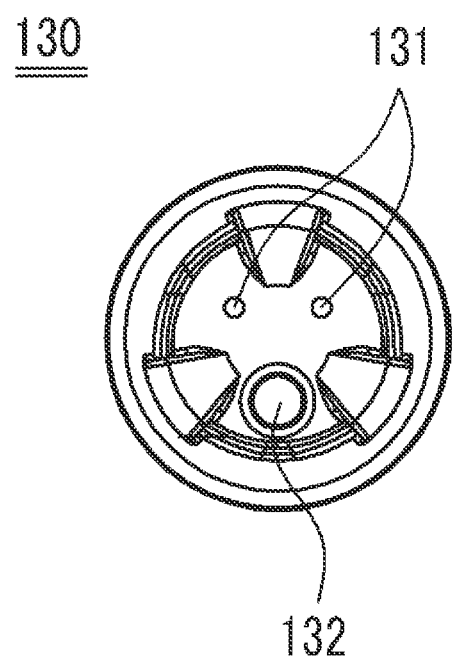
Figure 5A:
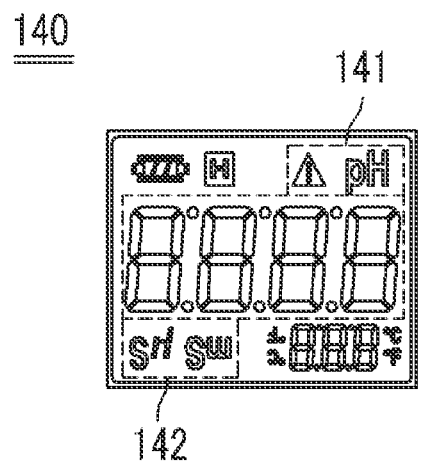
FIGS. 5A, 5B, and 5C are front views of a display module that is a main part of FIG. 2 and display units.
Figure 5B:
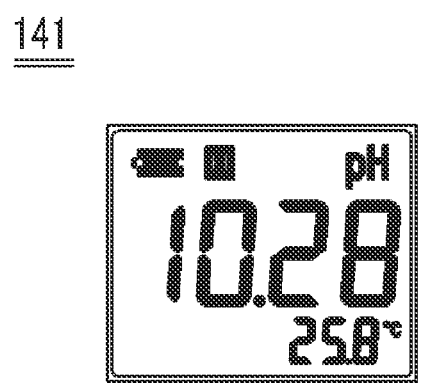
Figure 5C:
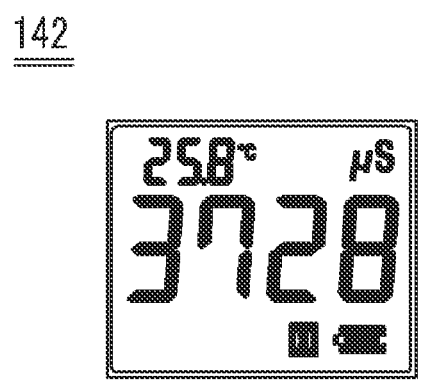

FIG. 2 is a front view of a water quality measuring apparatus according to an embodiment of the present invention, FIG. 3 is a block diagram illustrating constitutions of the water quality measuring apparatus according to an embodiment of the present invention, FIGS. 4A and 4B are side views of an acidity measuring module and an electric conductivity measuring module, respectively, which are main parts of FIG. 2. FIGS. 5A, 5B, and 5C are front views of a display module that is a main part of FIG. 2 and display units. In descriptions of the present invention, the same or similar parts are denoted by the same reference numerals although they are differently shown.

As illustrated in FIGS. 2 and 3, a water quality measuring apparatus 100 according to the present invention includes a bar-shaped housing 110 having a predetermined length, an acidity measuring module 120 (hereinafter, referred to as a "pH measuring module") disposed on one end of the housing 110, an electric conductivity measuring module 130 (hereinafter, referred to as an "EC measuring module") disposed on the other end of the housing 110, and a display module 140 disposed on an outer circumferential surface of the housing 110. Also, an inclination direction detection sensor 150 for detecting an inclined direction of the water quality measuring apparatus 100, a control module 160 for controlling operations of the pH measuring module 120 and the EC measuring module 130 and a display operation of the display module 140, and a power source module 170 providing a power for operating the water quality measuring apparatus 100 are built in the housing 110. Also, a manipulation unit 180 for inputting a user command is disposed on an outer circumferential surface of the housing 110. In the water quality measuring apparatus 100 including the above-described constitutions, a protection cap (see reference numeral 190 of FIGS. 6 and 7) may be coupled to the housing 110 outside the pH measuring module 120 and the EC measuring module 130 to protect the measuring modules 120 and 130.

Here, the housing 110 may provide a main body of the measuring apparatus 100 for accommodating the various constitutions therein. For this, the housing 110 may have an accommodation space therein and a bar type having a predetermined length. Also, the housing 110 may have a circular or oval shape in cross-section to allow a user to grasp the housing 110. Also, the housing 110 may be injection-molded by using a plastic material. The pH measuring module 120, the EC measuring module 130, and the display module 140 may be coupled to the inside and outside of the housing 110 to maintain sealing of the housing 110.

The pH measuring module 120 may be a part for measuring acidity (i.e., hydrogen ion concentration) of water to be measured (hereinafter, referred to as "measured water"). Here, a pH meter that measures acidity by using a voltage outputted according to a change in hydrogen ion concentration inside and outside a hydrogen sensitive glass bulb may be used as the pH measuring module 120. For this, as illustrated in FIG. 4A, the pH measuring module 120 may include a pH sensor electrode 121 including a measuring electrode and a reference electrode. Also, the pH measuring module 120 may further include a temperature sensor electrode 122 for measuring a temperature of the measured water to compensate a pH value according to the temperature of the measured water. The pH measuring module 120 may be coupled to one end of the housing 110. Also, the pH measuring module 120 may be connected to the control module 160 that is provided within the housing 110 to operate according to a control signal of the control module 160.

The EC measuring module 130 may be a part for measuring electric conductivity of the measured water. Here, an EC meter applying current between both electrodes to measure electric conductivity by using resistance generated in a solution of the measured water may be used as the EC measuring module 130. For this, as illustrated in FIG. 4B, the EC measuring module 130 may include an EC sensor electrode 131 including a pair of conductive electrodes that are spaced a predetermined distance from each other. Here, a temperature sensor electrode 132 for measuring a temperature of the measured water to compensate an EC value according to the temperature of the measured water. The EC measuring module 130 may be coupled to the other end (i.e., a side opposite to the pH measuring module) of the housing 110 to operate according to a control signal of the control module 160.

The display module 140 may be a part for displaying the acidity and electric conductivity which are measured by the pH measuring module 120 and the EC measuring module 130. Here, the acidity and electric conductivity may be alternately displayed on one display window. For this, a pH display unit 141 and an EC display unit 142 may be displayed on the display window at the same time. Particularly, as illustrated in FIG. 5C, the pH display unit 141 and the EC display unit 142 may be disposed so that the display units that are capable of mutually displaying the measured values overlap each other and are displayed in reverse directions. That is, as illustrated in FIG. 5B, the acidity may be displayed by the pH display unit 141 in one direction, and as illustrated FIG. 5C, the electric conductivity may be displayed by the EC display unit 142 in the other opposite direction.

The inclination direction detection sensor 150 may be a part for detecting whether the water quality measuring apparatus 100 is in an acidity measuring mode or electric conductive measuring mode with respect to the pH measuring module 120 and EC measuring module 130, which are spaced apart from each other at both ends of the housing 110. Since the water quality measuring apparatus has a predetermined length and both ends to which the pH measuring module 120 and the EC measuring module 130 are coupled, the water quality measuring apparatus (i.e., housing) may be inclined in a specific direction to measure the acidity and electric conductivity. Thus, the inclination direction detection sensor 150 may detect an inclined direction of the housing 110 to detect whether the water quality measuring apparatus is in the acidity measuring mode or electric conductivity measuring mode. A gyro sensor may be used as the inclination direction detection sensor 150. The inclination direction detection sensor 150 may be disposed within the housing 110 to detect an inclination and direction of the housing 110.

The power source module 170 may be a part for supplying a power required for operating the devices such as the pH measuring module 120, the EC measuring module 130, the display module 140, and the control module 160. The power source module 170 may be directly connected to an external power source. However, the power source module 170 may be provided as a general changeable battery or a charging module that is chargeable by using the external power source.

The control module 160 may be a part for controlling an overall operation of the water quality measuring apparatus. That is, the control module 160 may control the pH measuring module 120 and the EC measuring module 130 to measure the acidity and electric conductivity and compensate the measured values according to the temperature, thereby displaying the compensated values through the display module 140. Particularly, the pH measuring module 120 and the EC measuring module 130 may operate according to the inclined direction of the water quality measuring apparatus, which is detected by the inclination direction detection sensor 150, and simultaneously, the measured values may be displayed through the pH display unit 141 or the EC display unit 142. That is, when the control module 160 determines that the water quality measuring apparatus is in the acidity measuring mode according to the detected result of the inclination direction detection sensor 150, the control module 160 may control an operation of the pH sensor electrode 121 through a pH power source control unit 123. Also, when the control module 160 determines that the water quality measuring apparatus is in the electric conductivity measuring mode, the control module 160 may control an operation of the EC sensor electrode 131 through an EC power source control unit 133. The control module 160 may include a central processing unit 161 for controlling an operation of each device, an AD converter 162 for converting the values measured by the pH measuring module 120 and the EC measuring module 130 into digital values, and a memory 163 for storing various data.

The manipulation unit 180 may be a part for inputting a control command by the user. The manipulation unit 180 may include a button switch for turning on/off the water quality measuring apparatus 100.

Figure 6:
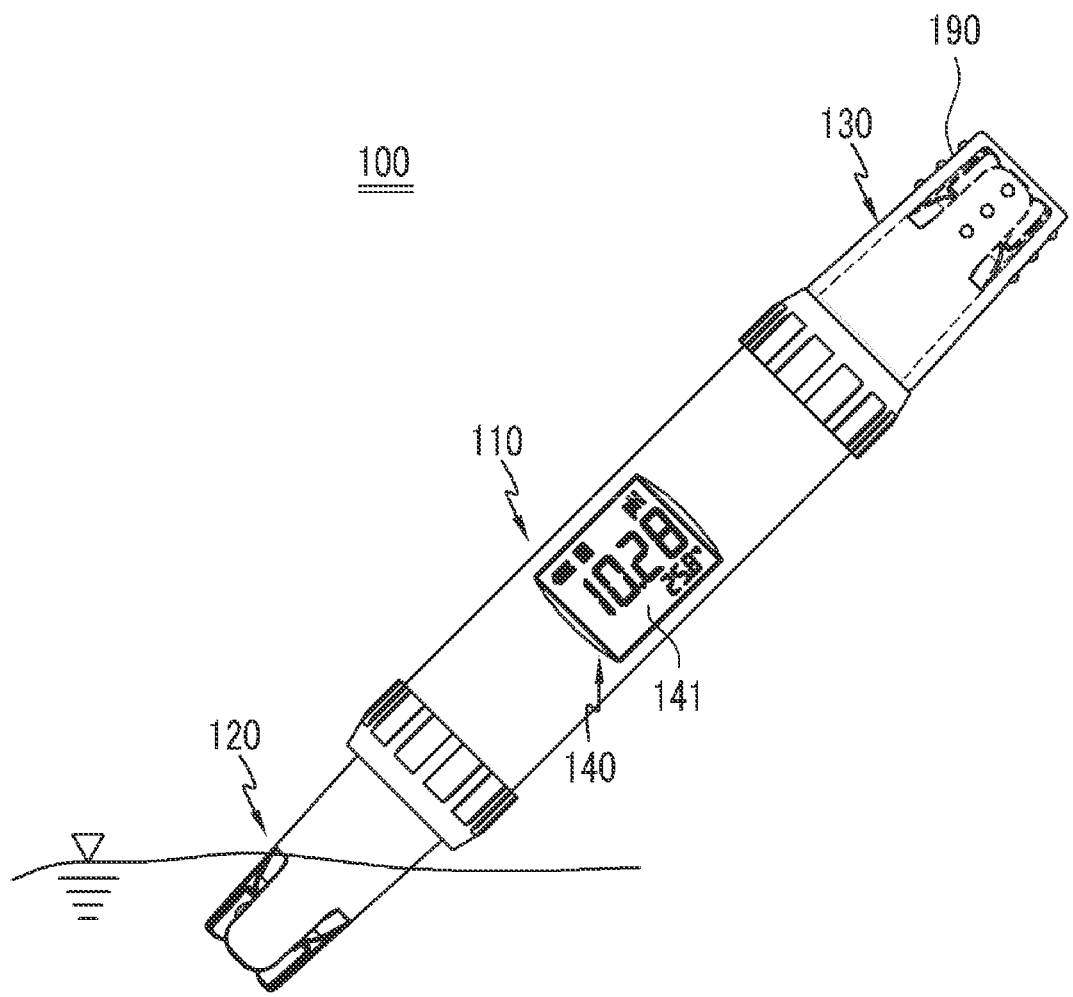
FIG. 6 is a view illustrating an acidity measuring state using the water quality measuring apparatus of FIG. 2.
Figure 7:
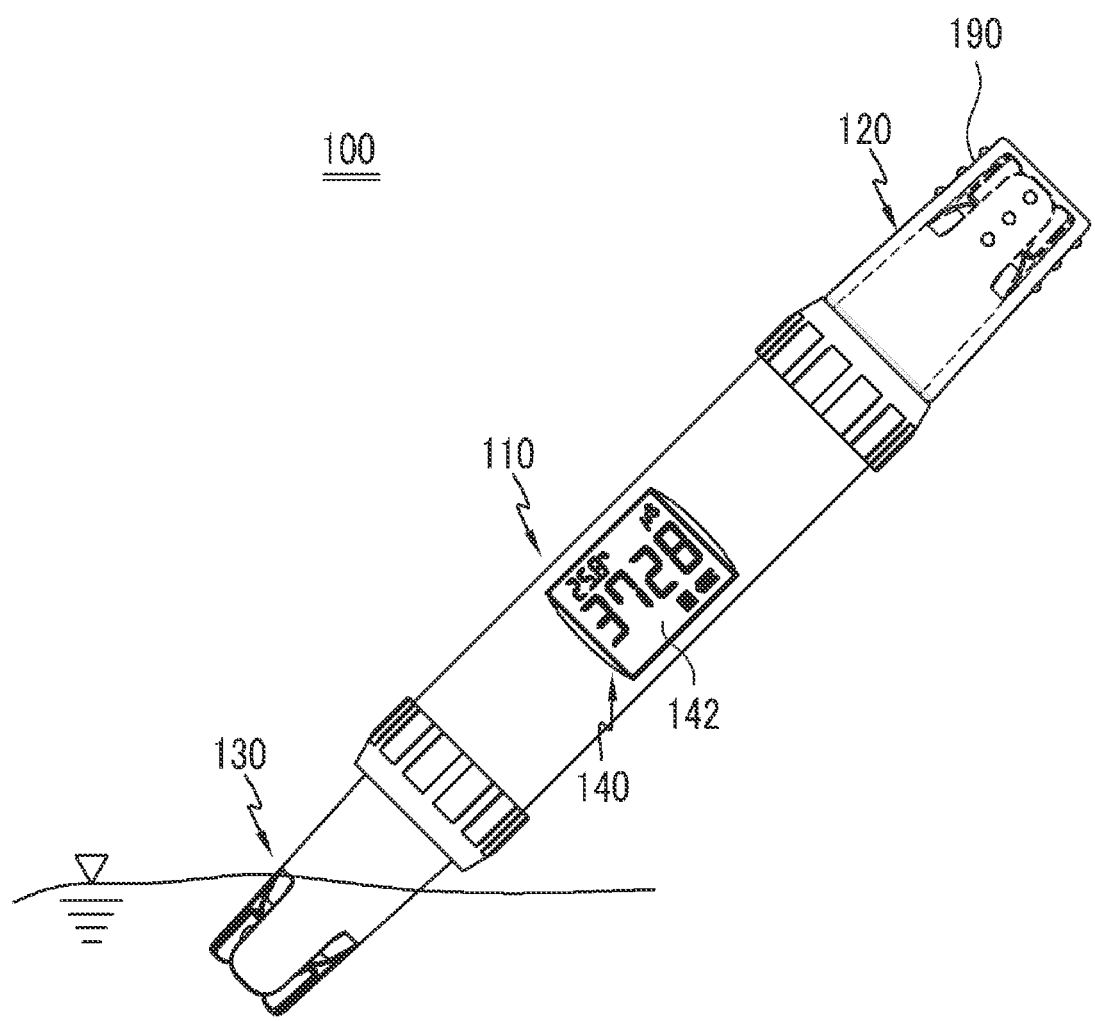
FIG. 7 is a view illustrating an electric conductivity measuring state using the water quality measuring apparatus of FIG. 2.

FIG. 6 is a view illustrating an acidity measuring state using the water quality measuring apparatus of FIG. 2, and FIG. 7 is a view illustrating an electric conductivity measuring state using the water quality measuring apparatus of FIG. 2.

As illustrated in FIG. 6, when it is intended to measure the acidity of the measured water, the user may immerse the pH measuring module 120 disposed at one side into the measured water. Here, the pH measuring module 120 of the water quality measuring apparatus 100 may be inclined downward. Here, the inclination direction detection sensor 150 may detect whether the water quality measuring apparatus 100 is in the acidity measuring mode by the inclined direction, and the control module 160 may operate the pH measuring module 120 according to the signal detected by the inclination direction detection sensor 150 to measure acidity of the measured water, thereby displaying the measured result on the pH display unit 141 of the display module 140.

Similarly, as illustrated in FIG. 7, when it is intended to measure the electric conductivity of the measured water, the user may immerse the EC measuring module 130 disposed at the other side into the measured water. Here, the EC measuring module 130 of the water quality measuring apparatus 100 may be inclined downward. Here, the inclination direction detection sensor 150 may detect whether the water quality measuring apparatus 100 is in the electric conductivity measuring mode by the inclined direction, and the control module 160 may operate the EC measuring module 130 according to the signal detected by the inclination direction detection sensor 150 to measure electric conductivity of the measured water, thereby displaying the measured result on the EC display unit 142 of the display module 140.

As described above, in the water quality measuring apparatus 100, the pH measuring module 120 and the EC measuring module 130 may be coupled to both sides of the housing 110 without interfering with each other to measure accurate values. Since the values corresponding to the acidity and the electric conductivity which are measured in the opposite directions are displayed in the opposite directions, the user may easily confirm the measured value in the each mode.

In the descriptions of the present invention, although the pH measuring module and the EC measuring module are exemplified as the measuring modules, the present invention is not limited thereto. For example, the pH measuring module and the EC measuring module may be substituted with a pair of measuring modules for measuring different characteristics to various characteristics of the water quality.

According to the present invention, since the first measuring module (the pH measuring module) and the second measuring module (the EC measuring module) for measuring the water quality characteristics different from each other are disposed on both ends of the housing in a longitudinal direction, each of the measuring modules may accurately measure the water quality without interfering with each other because interruption factors generated from the pH electrode sensor preservation solution and the conductive solution discharged from the reference are removed.

Also, the first and second measuring modules may be selectively operated in the inclined direction of the measuring apparatus by the inclination direction detection sensor without performing a separate manipulation to measure the corresponding water quality characteristic.

Also, the first and second display units for displaying the values measured by the first and second measuring modules are disposed to turn around and overlap each other. Also, while the first and second display units are inclined in directions different from each other, the value measured by the first and second measuring modules may be respectively displayed on the corresponding display units. Thus, the user may easily confirm the measured values.

Also, it may be unnecessary to provide separate devices for measuring the acidity and electric conductivity.

Accordingly, a person having ordinary skill in the art will understand from the above that various modifications and other equivalent embodiments are also possible.

What is claimed is:

1. A pen type of apparatus for measuring multiple water qualities, the apparatus comprising:
a housing having an accommodation space therein and a predetermined length;
a first measuring module disposed on a first distal end of the housing, wherein the first measuring module comprises an acidity measuring module that extends in a longitudinal direction of the housing and is adapted to measure acidity of water;
a second measuring module disposed on a second distal end of the housing that is opposite the first distal end, wherein the second measuring module includes an electric conductivity measuring module that extends in the longitudinal direction of the housing and is adapted to measure electric conductivity of the water;
an inclination direction detection sensor accommodated in the housing to detect an inclined direction of the housing;
a display module disposed on an outer circumferential surface of the housing to display values measured by the first and second measuring modules, wherein a first display unit for displaying the value measured by the first measuring module is disposed in one direction, and a second display unit for displaying the value measured by the second measuring module in the other opposite direction to overlap each other; and
a control module, accommodated in the housing, for controlling the first and second measuring modules such that the first and second measuring modules are selectively operated depending on the inclined direction of the housing, which inclined direction is detected by the inclination direction detection sensor in order to measure either one of the acidity or the electric conductivity of the water, the control module controlling the display module so that each of the values measured by the first and second measuring modules is displayed on the display module through the first or second display units,
wherein the first and second measuring modules are respectively disposed on the first and second distal ends of the housing to measure the water qualities different from each other and without interfering with each other.

2. The apparatus of claim 1, wherein the inclination direction detection sensor comprises a gyro sensor.

3. The apparatus of claim 1, further comprising a manipulation unit disposed on the outer circumferential surface to input a user command.

* * * * *